(12) United States Patent
    Corl

(10) Patent No.: US 11,224,403 B2
(45) Date of Patent: Jan. 18, 2022

(54) INTRAVASCULAR ULTRASOUND IMAGING APPARATUS, INTERFACE ARCHITECTURE, AND METHOD OF MANUFACTURING

(71) Applicant: Volcano Corporation, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1109 days.

(21) Appl. No.: 14/812,792

(22) Filed: Jul. 29, 2015

(65) Prior Publication Data
    US 2016/0029999 A1    Feb. 4, 2016

Related U.S. Application Data

(60) Provisional application No. 62/032,368, filed on Aug. 1, 2014.

(51) Int. Cl.
    *A61B 8/08*    (2006.01)
    *A61B 8/00*    (2006.01)
    (Continued)

(52) U.S. Cl.
    CPC ............... *A61B 8/12* (2013.01); *A61B 8/445* (2013.01); *A61B 8/4494* (2013.01);
    (Continued)

(58) Field of Classification Search
    CPC ......... A61B 8/12; A61B 8/445; A61B 8/4494; A61B 8/5207; A61B 8/56; B06B 1/0633
    See application file for complete search history.

(56) References Cited

U.S. PATENT DOCUMENTS 4,917,097 A    4/1990  Proudian
6,641,540 B2   11/2003 Fleischman et al.
               (Continued)

OTHER PUBLICATIONS

Isarakorn "Epitaxial Piezoelectric MEMS on Silicon" Ecole Polytechnique Federale Dde Lausanne. 2011.*

*Primary Examiner* — Michael T Rozanski

(57) ABSTRACT

Solid-state ultrasound imaging devices, systems, and methods are provided. Some embodiments of the present disclosure are particularly directed to compact and efficient ultrasound transducer scanner formed from a substantially cylindrical semiconductor substrate. In some embodiments, an intravascular ultrasound (IVUS) device includes: an ultrasound scanner assembly disposed at a distal portion of the flexible elongate member, the ultrasound scanner assembly including a semiconductor substrate having a plurality of transistors formed thereupon. The semiconductor substrate is curved to have a substantially cylindrical form when the ultrasound scanner assembly is in a rolled form, and the plurality of transistors are arranged in a cylindrical arrangement when the ultrasound scanner assembly is in the rolled form. In one such embodiment, the device further includes a plurality of ultrasound transducers formed upon the semiconductor substrate and arranged in a cylindrical arrangement when the ultrasound scanner assembly is in the rolled form.

19 Claims, 16 Drawing Sheets

(51) Int. Cl.
*A61B 8/12* (2006.01)
*B06B 1/06* (2006.01)

(52) U.S. Cl.
CPC .......... *A61B 8/5207* (2013.01); *B06B 1/0633* (2013.01); *A61B 8/56* (2013.01)

(56) References Cited

U.S. PATENT DOCUMENTS

| | | | |
|---|---|---|---|
| 6,776,763 B2 | 8/2004 | Nix et al. | |
| 7,226,417 B1 | 6/2007 | Eberle et al. | |
| 7,846,101 B2 | 12/2010 | Eberle et al. | |
| 2005/0146247 A1 | 7/2005 | Fisher | |
| 2007/0016020 A1 | 1/2007 | Oshiki | |
| 2007/0264732 A1* | 11/2007 | Chen | A61B 1/041 438/22 |
| 2010/0262014 A1* | 10/2010 | Huang | A61B 8/12 600/466 |
| 2010/0280388 A1* | 11/2010 | Huang | A61B 8/12 600/459 |
| 2013/0208572 A1* | 8/2013 | Klee | B06B 1/0622 367/180 |
| 2013/0310679 A1 | 11/2013 | Natarajan | |

* cited by examiner

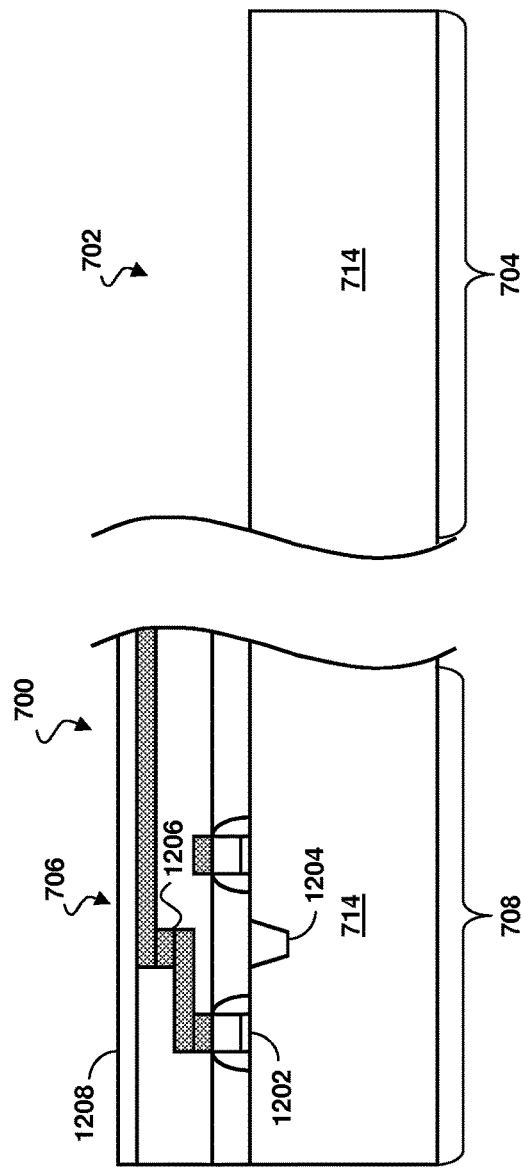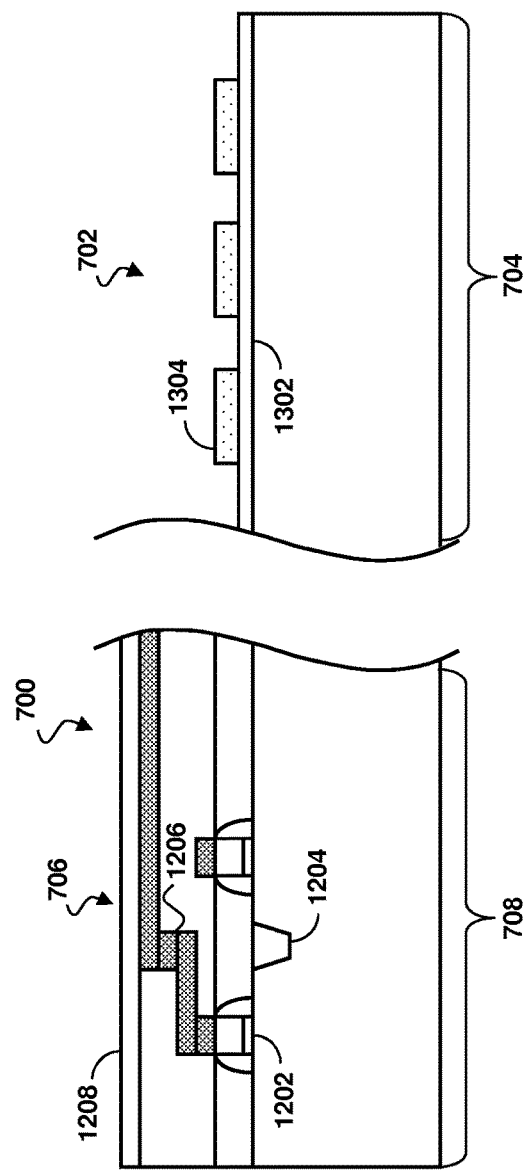

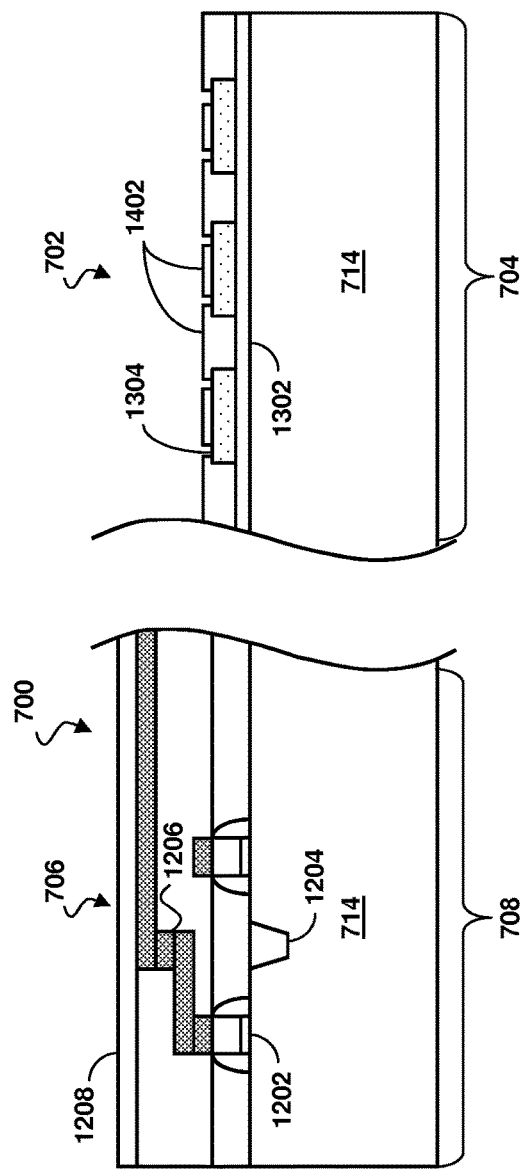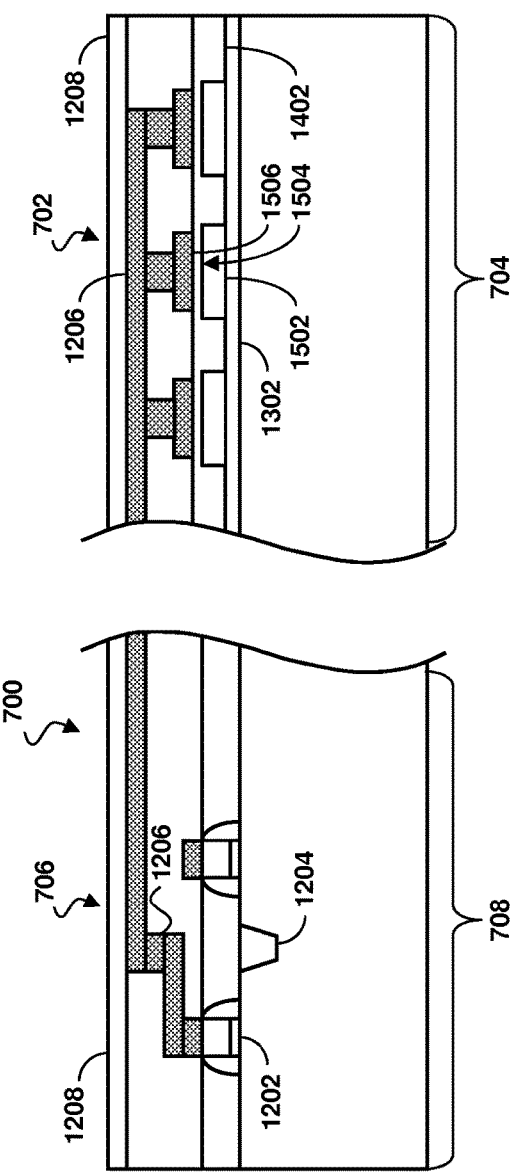
Fig. 14
Fig. 15

INTRAVASCULAR ULTRASOUND IMAGING APPARATUS, INTERFACE ARCHITECTURE, AND METHOD OF MANUFACTURING

CROSS-REFERENCE TO RELATED APPLICATIONS

The present application claims priority to and the benefit of U.S. Provisional Patent Application No. 62/032,368, filed Aug. 1, 2014, which is hereby incorporated by reference in its entirety.

TECHNICAL FIELD

The present disclosure relates generally to intravascular ultrasound (IVUS) imaging and, in particular, to a solid-state IVUS imaging system. In various embodiments, the IVUS imaging system includes an array of ultrasound transducers, such as piezoelectric zirconate transducers (PZTs), capacitive micromachined ultrasonic transducers (CMUTs), and/or piezoelectric micromachined ultrasound transducers (PMUTs), formed on a semiconductor substrate along with associated control logic. The semiconductor substrate is then rolled into a cylindrical form to form a scanner assembly and disposed at a distal end of an intravascular elongate member. The resulting device is suitable for advancing into an enclosed space and imaging the surrounding structures. For example, some embodiments of the present disclosure provide an IVUS imaging system particularly suited to imaging a human blood vessel.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device includes one or more ultrasound transducers arranged at a distal end of an elongate member. The elongate member is passed into the vessel thereby guiding the transducers to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS devices utilize a scanner assembly that includes an array of ultrasound transducers distributed around the circumference of the device connected to a set of transducer controllers. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

Because an IVUS device is advanced into a confined space, device agility, which strikes a balance between flexibility and controllability, is an important characteristic. Rotational devices tend to smoothly advance around corners due to the flexible rotating drive shaft contained within the sheath. However, rotational IVUS devices often require a long rapid exchange tip to engage the guidewire, and the long tip may limit the advance of the imaging core containing the transducer. For example, this may prevent the device from being advanced to very distal locations within the coronary arteries. On the other hand, solid-state IVUS devices may have a shorter tip as the guidewire can pass through the interior lumen of the scanner. However, some solid-state designs have rigid segments that limit the ability to advance the elongate member around sharp bends in the vasculature. Solid-state IVUS devices also tend to be larger in diameter than rotational devices to accommodate the transducer array and the associated electronics.

While existing IVUS imaging systems have proved useful, there remains a need for improvements in the design of the solid-state scanner to reduce its overall diameter and to reduce the length of rigid portions of the elongate member in order to provide improved access to the vasculature. In addition, the improvements to fabrication and assembly techniques would also prove beneficial because of the difficulties inherent in assembling miniscule components. Accordingly, the need exists for improvements to the scanner assembly and its components, and to the methods used in manufacturing these elements.

SUMMARY

Embodiments of the present disclosure provide a compact and efficient scanner assembly in a solid-state imaging system.

In some embodiments, an intravascular ultrasound (IVUS) device is provided. The device comprises: a flexible elongate member; and an ultrasound scanner assembly disposed at a distal portion of the flexible elongate member, the ultrasound scanner assembly including a semiconductor substrate having a plurality of transistors formed thereupon, wherein the semiconductor substrate is curved to have a substantially cylindrical form when the ultrasound scanner assembly is in a rolled form, and wherein the plurality of transistors are arranged in a cylindrical arrangement when the ultrasound scanner assembly is in the rolled form. In one example, the device further comprises: a plurality of ultrasound transducers formed upon the semiconductor substrate and electrically coupled to the transducer control circuitry, wherein the plurality of ultrasound transducers are arranged in a cylindrical arrangement when the ultrasound scanner assembly is in the rolled form.

In some embodiments, a scanner assembly for ultrasound imaging is provided. The scanner assembly comprises a rollable semiconductor substrate; transducer control logic formed on a control region of the rollable semiconductor substrate; and a transducer formed on a transducer region of the rollable semiconductor substrate and electrically coupled to the transducer control logic, wherein the transducer control logic and the transducer have a curved form. In one such embodiment, the rollable semiconductor substrate includes a silicon semiconductor having a curved form.

In some embodiments, a method of manufacturing an intravascular ultrasound device is provided. The method comprises: receiving a semiconductor substrate; forming a transistor on the semiconductor substrate; forming an ultrasound transducer on the semiconductor substrate; and rolling the semiconductor substrate having the transistor and the ultrasound transducer formed thereupon to have a substantially cylindrical form, wherein the rolling changes the profile of each of the transistor and the ultrasound transducer. In one example, the method further comprises: performing a process to change the semiconductor substrate from a rigid state to a rollable state prior to the rolling of the semiconductor substrate.

Some embodiments of the present disclosure utilize improved fabrication techniques to reduce the diameter and length of the scanner assembly. As the scanner assembly is rigid, decreasing the size creates a more responsive device and may allow for a thinner elongate member. The dimensions of a conventional scanner assembly may be determined in part by the geometric challenges of arranging flat elements such as controllers and transducers into a roughly cylindrical device as well as the need for a transition zone to accommodate differences in the cross-sectional shape along the length of the cylinder. In contrast, in some embodiments of the present disclosure, the transducers and control logic are formed on a rollable substrate. During the rolling stage, the entire substrate including the transducers and the control logic can be curved to form a more cylindrical device. By utilizing space more efficiently, the rollable substrate increases the device density and decreases the size of the scanner assembly. By forming a more uniform profile, the rollable substrate may permit a shorter transition zone, further decreasing the length of the scanner assembly along the longitudinal axis of the rolled assembly. The resulting IVUS device is narrower and more flexible and, therefore, able to maneuver through complicated vascular branches.

Some embodiments leverage the advantages of manufacturing the elements of the scanner assembly on a single semiconductor substrate to further reduce device size. Instead of dividing the elements into discrete dies, separating the dies, and reassembling them on a flexible interconnect, in the present embodiments, the elements remain together on the semiconductor substrate throughout the manufacture of the scanner assembly. This eliminates the packaging bulk associated with multiple dies and may result in more reliable interconnections. Furthermore, the yield loss associated with dicing tiny components and bonding them to a flexible interconnect is avoided. As a result, the manufacturing technique simplifies assembly, reduces assembly time, and improves both yield and device reliability.

Additional embodiments incorporate transducers that are specially adapted to a flexible substrate. The transducers are formed from an array of diaphragms or drumheads. As some flexible substrates are relatively thin, the resonance chamber of each diaphragm may be shallow. However, by connecting several diaphragms in parallel, the effective size is much larger. This allows the transducer to provide a more powerful ultrasonic signal while transmitting and to produce a stronger electrical signal while receiving. In addition, the operational frequency of a transducer can be tuned by adjusting the number of diaphragms operating in parallel. The result is a more sensitive transducer in a smaller package.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 12-16 are cross-sectional views of a scanner assembly being manufactured by the method according to an embodiment of the present disclosure.

DETAILED DESCRIPTION

Figure 1:
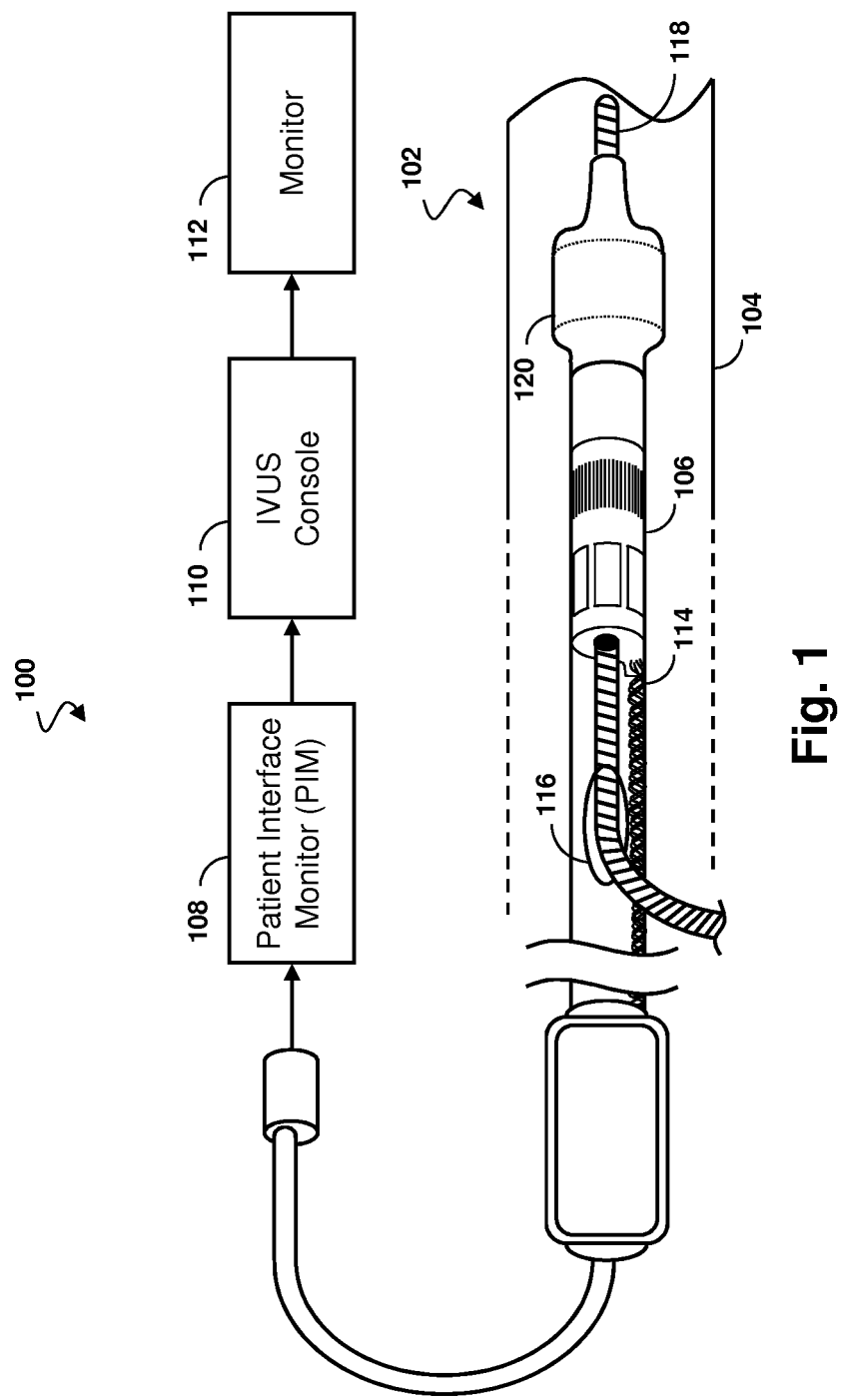
FIG. 1 is a diagrammatic schematic view of an intravascular ultrasound (IVUS) imaging system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the IVUS system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100 according to an embodiment of the present disclosure. At a high level, an elongate member 102 (such as a catheter, guide wire, or guide catheter) of the imaging system 100 is advanced into a vessel 104. The distal-most end of the elongate member 102 includes a scanner assembly 106 with an array of ultrasound transducers and associated control circuitry. When the scanner assembly 106 is positioned near the area to be imaged, the ultrasound transducers are activated and ultrasonic energy is produced. A portion of the ultrasonic energy is reflected by the vessel 104 and the surrounding anatomy and received by the transducers. Corresponding echo information is passed along through a Patient Interface Monitor (PIM) 108 to an IVUS console 110, which renders the information as an image for display on a monitor 112.

The imaging system 100 may use any of a variety of ultrasonic imaging technologies. Accordingly, in some embodiments of the present disclosure, the IVUS imaging system 100 is a solid-state IVUS imaging system incorporating an array of piezoelectric transducers fabricated from lead-zirconate-titanate (PZT) ceramic. In some embodiments, the system 100 incorporates capacitive micromachined ultrasonic transducers (CMUTs), or piezoelectric micromachined ultrasound transducers (PMUTs).

In some embodiments, the IVUS system 100 includes some features similar to traditional solid-state IVUS system, such as the EagleEye® catheter available from Volcano Corporation and those disclosed in U.S. Pat. No. 7,846,101 hereby incorporated by reference in its entirety. For example, the elongate member 102 includes the ultrasound scanner assembly 106 at a distal end of the member 102, which is coupled to the PIM 108 and the IVUS console 110 by a cable 114 extending along the longitudinal body of the member 102. The cable 114 caries control signals, echo data, and power between the scanner assembly 106 and the remainder of the IVUS system 100.

In an embodiment, the elongate member 102 further includes a guide wire exit port 116. The guide wire exit port 116 allows a guide wire 118 to be inserted towards the distal end in order to direct the member 102 through a vascular structure (i.e., a vessel) 104. Accordingly, in some instances the IVUS device is a rapid-exchange catheter. In an embodiment, the elongate member 102 also includes an inflatable balloon portion 120 near the distal tip. The balloon portion 120 is open to a lumen that travels along the length of the IVUS device and ends in an inflation port (not shown). The balloon 120 may be selectively inflated and deflated via the inflation port.

The PIM 108 facilitates communication of signals between the IVUS console 110 and the elongate member 102 to control the operation of the scanner assembly 106. This includes generating control signals to configure the scanner, generating signals to trigger the transmitter circuits, and/or forwarding echo signals captured by the scanner assembly 106 to the IVUS console 110. With regard to the echo signals, the PIM 108 forwards the received signals and, in some embodiments, performs preliminary signal processing prior to transmitting the signals to the console 110. In examples of such embodiments, the PIM 108 performs amplification, filtering, and/or aggregating of the data. In an embodiment, the PIM 108 also supplies high- and low-voltage DC power to support operation of the circuitry within the scanner assembly 106.

The IVUS console 110 receives the echo data from the scanner assembly 106 by way of the PIM 108 and processes the data to create an image of the tissue surrounding the scanner assembly 106. The console 110 may also display the image on the monitor 112.

The ultrasound imaging system 100 may be utilized in a variety of applications and can be used to image vessels and structures within a living body. Vessel 104 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include imaging man-made structures such as, but without limitation, heart valves, stents, shunts, filters and other devices positioned within the body.

Figure 2:
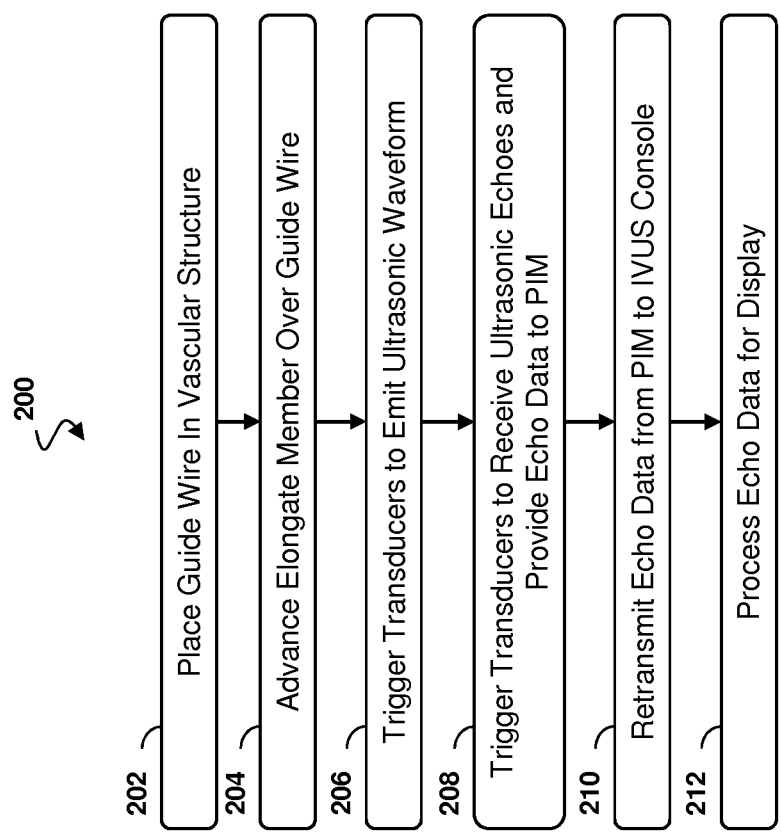
FIG. 2 is a flow diagram of a method of utilizing the IVUS system according to an embodiment of the present disclosure.

FIG. 2 is a flow diagram of a method 200 of utilizing the IVUS system 100 according to an embodiment of the present disclosure. It is understood that additional steps can be provided before, during, and after the steps of method 200, and that some of the steps described can be replaced or eliminated for other embodiments of the method.

Referring block 202 of FIG. 2 and referring still to FIG. 1, in an illustrative example of a typical environment and application of the system, a surgeon places a guide wire 118 in the vessel 104. The guide wire 118 is threaded through at least a portion of the distal end of the elongate member 102 either before, during, or after placement of the guide wire 118. Referring to block 204 of FIG. 2, once the guide wire 118 is in place, the elongate member 102 is advanced over the guide wire. Additionally or in the alternative, a guide catheter is advanced in the vessel 104 in block 202 and the elongate member 102 is advanced within the guide catheter in block 204. Referring to block 206, once positioned, the scanner assembly 106 is activated. Signals sent from the PIM 108 to the scanner assembly 106 via the cable 114 cause transducers within the assembly 106 to emit a specified ultrasonic waveform. The ultrasonic waveform is reflected by the vessel 104. Referring to block 208 of FIG. 2, the reflections are received by the transducers within the scanner assembly 106 and are amplified for transmission via the cable 114. The echo data is placed on the cable 114 and sent to the PIM 108. The PIM 108 amplifies the echo data and/or performs preliminary pre-processing, in some instances. Referring to block 210 of FIG. 2, the PIM 108 retransmits the echo data to the IVUS console 110. Referring to block 212 of FIG. 2, the IVUS console 110 aggregates and assembles the received echo data to create an image of the vessel 104 for display on the monitor 112. In some exemplary applications, the IVUS device is advanced beyond the area of the vessel 104 to be imaged and pulled back as the scanner assembly 106 is operating, thereby exposing and imaging a longitudinal portion of the vessel 104. To ensure a constant velocity, a pullback mechanism is used in some instances. A typical withdraw velocity is 0.5 mm/s. In some embodiments, the member 102 includes an inflatable balloon portion 120. As part of a treatment procedure, the device may be positioned adjacent to a stenosis (narrow segment) or an obstructing plaque within the vessel 104 and inflated in an attempt to widen the restricted area of the vessel 104.

The system 100, and in particular the elongate member 102, is designed to provide high-resolution imaging from within narrow passageways. To advance the performance of IVUS imaging devices compared to the current state of the art, embodiments of the present disclosure have improved flexibility and reduced diameter allowing greater maneuverability and leading to increased patient safety and comfort. While the elongate member 102 is generally flexible, it may include components within it that are not. For example, the ultrasound scanner assembly 106 is often rigid. As a result, the scanner assembly 106 may limit the agility of the elongate member 102 and may make navigating the vessel 104 more difficult. In addition, the bulk of the ultrasound transducers and the associated circuitry in the scanner assembly 106 may make it a limiting factor in the drive towards a smaller-gauge elongate member 102. For these reasons and others, an ultrasound scanner assembly 106 that is smaller longitudinally and circumferentially, as provided herein, may allow for a thinner elongate member 102 with improved agility to navigate complex vessels 104. Specific embodiments also provide faster, less expensive, and more reliable methods of manufacturing the scanner assembly 106.

Figure 3:
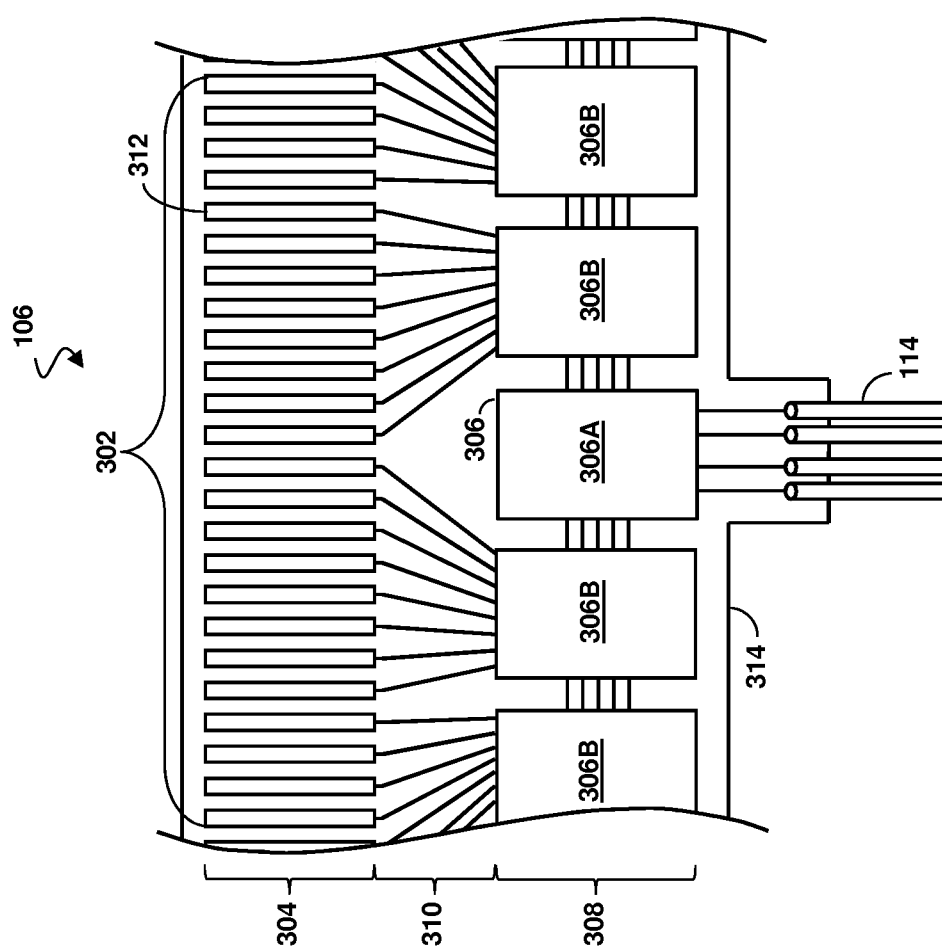
FIG. 3 is a top view of a portion of an ultrasound scanner assembly according to an embodiment of the present disclosure.

FIG. 3 is a top view of a portion of an ultrasound scanner assembly 106 according to an embodiment of the present disclosure. FIG. 3 depicts the ultrasound scanner assembly 106 in its flat form. The assembly 106 includes a transducer array 302 formed in a transducer region 304 and transducer control logic dies 306 (including dies 306A and 306B) formed in a control region 308, with a transition region 310 disposed therebetween. With respect to the transducer array 302, the array 302 may include any number and type of ultrasound transducers 312, although for clarity only a limited number of ultrasound transducers are illustrated in FIG. 3. In an embodiment, the transducer array 302 includes 64 individual ultrasound transducers 312. In a further embodiment, the transducer array 302 includes 32 ultrasound transducers 312. Other numbers are both contemplated and provided for. With respect to the types of transducers, in an embodiment, the ultrasound transducers 312 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric transducers fabricated from bulk PZT ceramic or single crystal piezoelectric material, piezoelectric micromachined ultrasound transducers (PMUTs), capacitive micromachined ultrasound transducers (CMUTs), other suitable ultrasound transmitters and receivers, and/or combinations thereof.

The scanner assembly 106 may include various transducer control logic, which in the illustrated embodiment is divided into discrete control logic dies 306. In various examples, the control logic of the scanner assembly 106 performs: decoding control signals sent by the PIM 108 across the cable 114, driving one or more transducers 312 to emit an ultrasonic signal, selecting one or more transducers 312 to receive a reflected echo of the ultrasonic signal, amplifying a signal representing the received echo, and/or transmitting the signal to the PIM across the cable 114. In the illustrated embodiment, a scanner assembly 106 having 64 ultrasound transducers 312 divides the control logic across nine control logic dies 306, of which five are shown. Designs incorporating other numbers of control logic dies 306 including 8, 9, 16, 17 and more are utilized in other embodiments. In general, the control logic dies 306 are characterized by the number of transducers they are capable of driving, and exemplary control logic dies 306 drive 4, 8, and 16 transducers.

The control logic dies are not necessarily homogenous. In some embodiments, a single controller is designated a master control logic die 306A and contains the communication interface for the cable 114. Accordingly, the master control circuit may include control logic that decodes control signals received over the cable 114, transmits control responses over the cable 114, amplifies echo signals, and/or transmits the echo signals over the cable 114. The remaining controllers are slave controllers 306B. The slave controllers 306B may include control logic that drives a transducer 312 to emit an ultrasonic signal and selects a transducer 312 to receive an echo. In the depicted embodiment, the master controller 306A does not directly control any transducers 312. In other embodiments, the master controller 306A drives the same number of transducers 312 as the slave controllers 306B or drives a reduced set of transducers 312 as compared to the slave controllers 306B. In an exemplary embodiment, a single master controller 306A and eight slave controllers 306B are provided with eight transducers assigned to each slave controller 306B.

The transducer control logic dies 306 and the transducers 312 are mounted on a flex circuit 314 that provides structural support and interconnects for electrical coupling. The flex circuit 314 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). The film layer is configured to be wrapped around a ferrule to form a cylindrical toroid in some instances. Therefore, the thickness of the film layer is generally related to the degree of curvature in the final assembled scanner assembly 106. In some embodiments, the film layer is between 5 μm and 100 μm, with some particular embodiments being between 12.7 μm and 25.1 μm.

To electrically interconnect the control logic dies 306 and the transducers, in an embodiment, the flex circuit 314 further includes conductive traces formed on the film layer that carry signals between the control logic dies 306 and the transducers 312 and that provide a set of pads for connecting the conductors of cable 114. Suitable materials for the conductive traces include copper, gold, aluminum, silver, nickel, and tin and may be deposited on the flex circuit 314 by processes such as sputtering, plating, and etching. In an embodiment, the flex circuit 314 includes a chromium adhesion layer or a titanium-tungsten adhesion layer. The width and thickness of the conductive traces are selected to provide proper conductivity and resilience when the flex circuit 314 is rolled. In that regard, an exemplary range for the width of a conductive trace is between 10-50 µm. For example, in an embodiment, 20 µm conductive traces are separated by 20 µm of space. The width of a conductive trace may be further determined by the size of a pad of a device or the width of a wire to be coupled to the trace. The thickness of the conductive traces may have a range from about 1 µm to about 10 µm, with a typical thickness of 5 µm.

In some instances, the scanner assembly 106 is transitioned from a flat configuration to a rolled or more cylindrical configuration. For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

Figure 4:
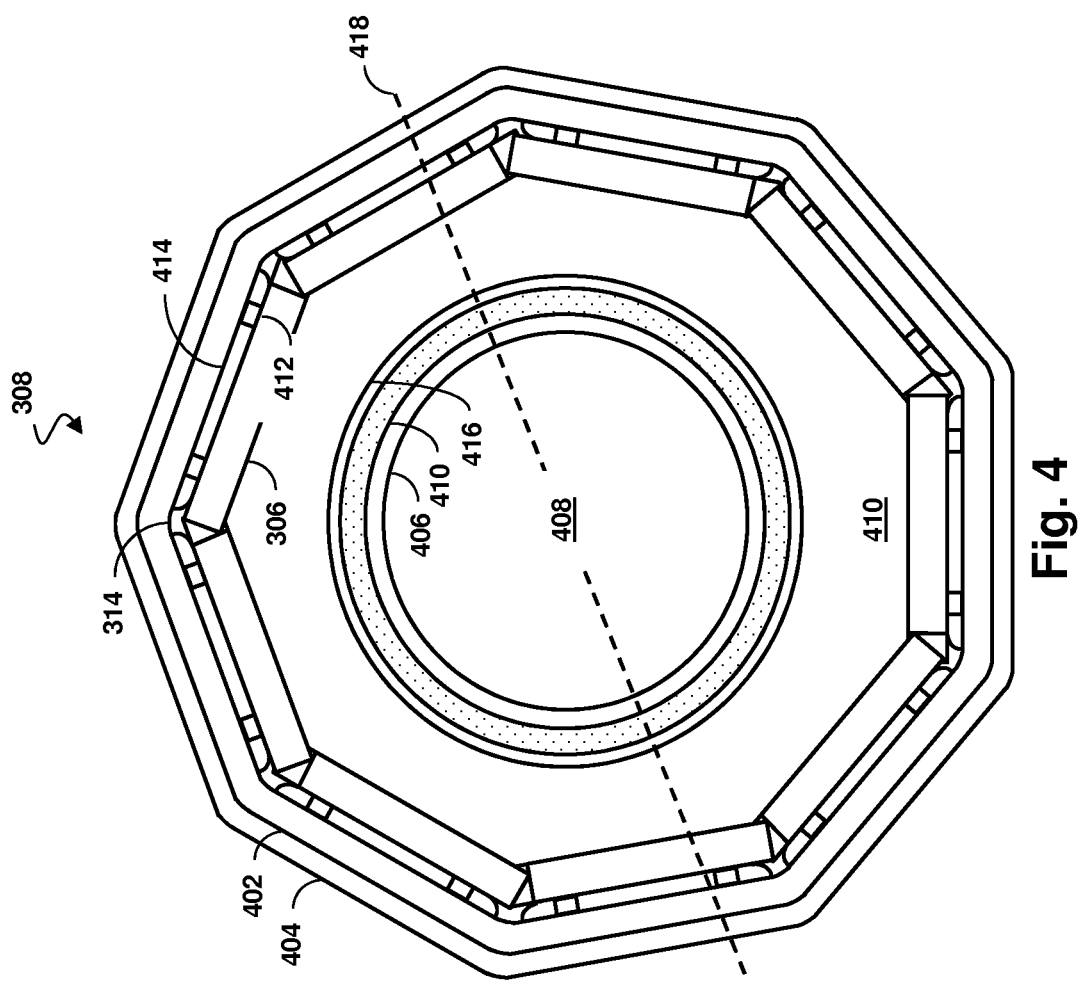
FIG. 4 is a cross-sectional view of a control region of an ultrasound scanner assembly according to an embodiment of the present disclosure.

FIG. 4 is a cross-sectional view of a control region 308 of an ultrasound scanner assembly 106 according to an embodiment of the present disclosure. The control region 308 is depicted in its rolled form and contains the transducer control logic dies 306 bonded to the flex circuit 314. In the illustrated embodiment, the flex circuit 314 also includes a conductive ground layer 402. In a further embodiment, the flex circuit includes an outer membrane 404 used to insulate and cover the ground layer 402 and to protect the scanner assembly 106 from the environment. Insulator materials for the outer membrane 404 may be selected for their biocompatibility, durability, hydrophilic or hydrophobic properties, low-friction properties, ultrasonic permeability, and/or other suitable criteria. For example, the outer membrane may include Parylene™ (trademark of Union Carbide). Other suitable materials include heat shrink tubing such as polyester or PVDF, a melt-formable layers such as Pebax® (registered trademark of Arkema) or polyethylene, and/or other suitable membrane materials.

As discussed above, in many embodiments, the flex circuit 314 and the attached elements are rolled around a ferrule 406. The lumen region 408 inside the ferrule 406 is open to allow the scanner assembly 106 to be advanced over a guide wire (not shown). The ferrule 406 may include a radiopaque material to aid in visualizing the scanner assembly 106 during a procedure. In some instances, encapsulating epoxy 410 fills the spaces between the control logic dies 306 and the ferrule 406.

In some embodiments, the control logic dies 306 are coupled to the flex circuit 314 by contact bumps 412. The contact bumps 412 may include a metal core, such as a copper core, with a solder portion. During formation, the contact may be heated, causing the solder to flow and join the metal core of the contact bump 412 to the flex circuit 314 trace. An underfill material 414 between the control logic dies 306 and the flex circuit 314 may be applied to increase the bond strength, to provide structural support for the control region 308, to insulate conductive structures including the contact bumps 412, and/or to promote thermal conduction.

In an embodiment, the control region 308 includes a retaining structure 416 applied over the transducer control logic dies 306. The retaining structure 416 may be used during the rolling process, for example, to secure components including the control logic dies 306. Encapsulating epoxy 410 fills the space between the transducer control logic dies 306 and the retaining structure 416 and between the retaining structure 416 and the ferrule 406 in some embodiments.

As can be seen from FIG. 4, the transducer control logic dies 306 at least partially define the shape of the control region 308. In the illustrated embodiment, because the transducer control logic dies 306 are rigid, the portions of the flex circuit 314 adjacent to the control logic dies 306 are relatively flat while the portions of the flex circuit adjacent gaps between the dies 306 are relatively rounded, resulting in a cross-sectional shape that is more polygonal than circular. As can be seen, the gaps between control logic dies 306 in the rolled configuration increase the effective diameter 418 of the control region 308. In some embodiments, half of the circumference of the control region 308 is due to gap space. The result is a larger and more irregular shaped scanner assembly 106.

To reduce the gap space, in some embodiments, the control logic dies 306 include interlocking teeth. For example, control logic dies 306 may be formed with a recess and projection that interlocks with a recess and projection of an adjacent control logic die 306 to form a box joint or finger joint. In the illustrated embodiment, each of the dies 306 interlocks with two adjacent controllers utilizing a recess and projection interface. In some embodiments, a control logic die 306 includes a chamfered edge, either alone or in combination with a recess and projection. The chamfered edge may be configured to abut an edge of an adjacent control logic die 306. In some such embodiments, the edge of the adjacent controller is chamfered as well. Other combinations, including embodiments utilizing a number of different mechanisms, are contemplated and provided for. Edge configurations that interlock adjacent control logic dies 306 may allow for closer control logic die spacing and a reduced diameter 418 in the rolled configuration. Such configurations may also interlock to create a rigid structure and thereby provide additional structural support for the rolled scanner assembly 106. Additionally or in the alternative, narrower and more numerous control logic dies 306 are used in place of larger dies in order to reduce the size of the flat areas of the controller region 308. It follows that designs utilizing 8, 9, 16, or more transducer control logic dies 306 have a more circular cross-section than designs with 4 or 5 controllers.

Figure 5:
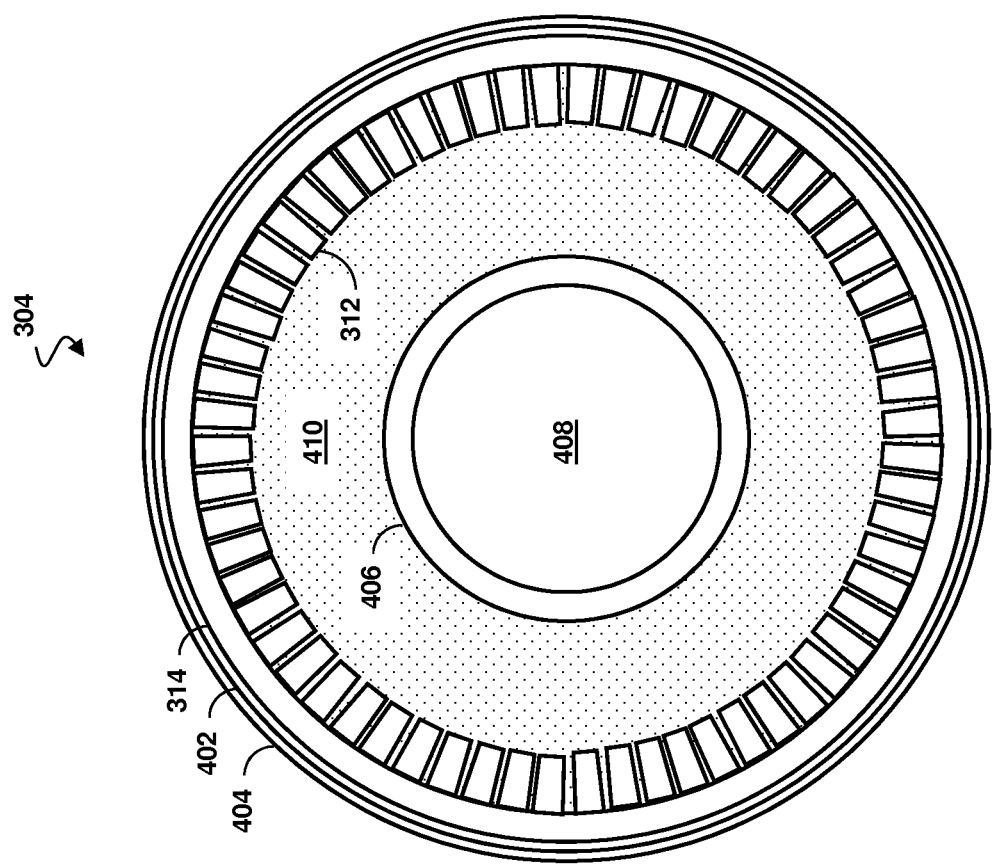
FIG. 5 is a cross-sectional view of a transducer region of an ultrasound scanner assembly according to an embodiment of the present disclosure.

FIG. 5 is a cross-sectional view of a transducer region 304 of an ultrasound scanner assembly 106 according to an embodiment of the present disclosure. The transducer region 304 is depicted in its rolled form. As the name implies, the transducer region 304 of the scanner contains the transducers 312, which, as previously disclosed, are physically attached to the flex circuit 314 and are electrically coupled to the traces of the flex circuit 314. As can be seen, the size, shape, and spacing of the ultrasound transducers 312 at least partially define the shape of the transducer region 304, with the portions of the flex circuit 314 that are adjacent to the transducers 312 being relatively flat and the portions of the flex circuit that are adjacent gaps between transducers 312 being relatively rounded. Due in part to the smaller size and greater number of transducers 312, the transducer region 304 may be more circular than the control region 308. In embodiments with 64 ultrasound transducers 312, the cross-section of the transducer region 304 is nearly circular.

Figure 6:
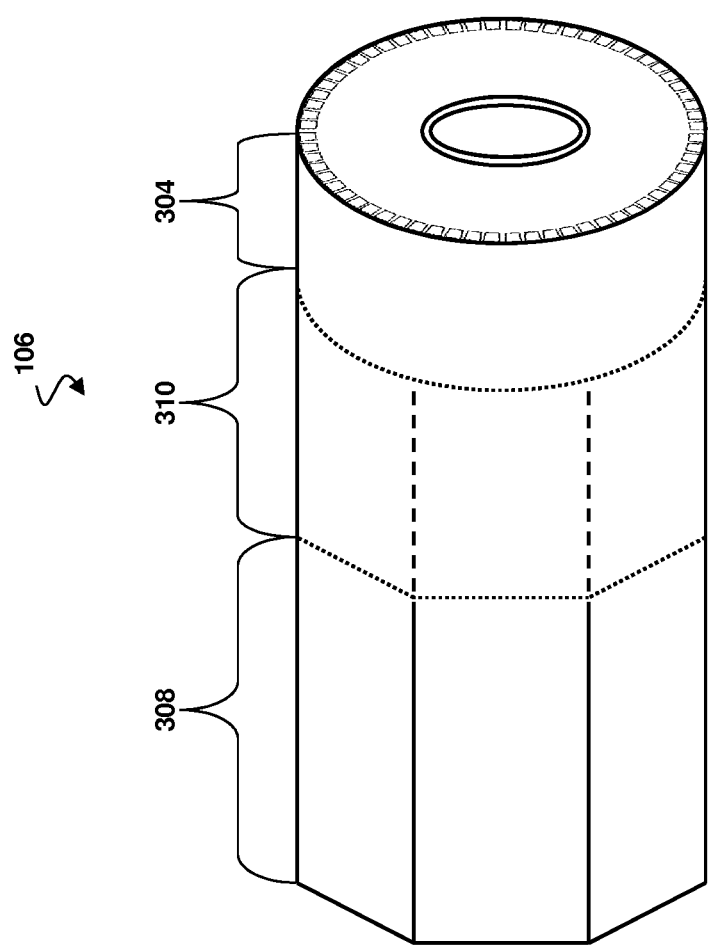
FIG. 6 is a longitudinal perspective view of a portion of an ultrasound scanner assembly depicted in its rolled form according to an embodiment of the present disclosure.

To accommodate the difference between the cross-sectional shapes of the transducer region 304 and the control region 308, the scanner assembly 106 may include a transition region 310 as shown in FIG. 6. FIG. 6 is a longitudinal perspective view of a portion of an ultrasound scanner assembly 106 depicted in its rolled form according to an embodiment of the present disclosure. Referring to FIG. 6, the transition region 310 is located between the transducer region 304 and the control region 308. In contrast to the transducer region 304 and the control region 308, the transition region 310 is free of rigid structures. Instead, the cross-sectional shape is defined by the adjacent regions 304 and 308. Thus, the shape of the transition region 310 transitions between that of the transducer region 304 and the controller region 308. The transition region 310 may be used to reduce sharp angles that can stress the flex circuit 314 and/or the conductive traces. Greater differences in cross-sectional shapes may result in a longer transition region 310. In an exemplary four-control logic die embodiment, the transition region 310 is approximately 1 to 1.5 catheter diameters in order to transition from square to substantially round. This works out to be between 1000 and 1500 µm for a 3Fr catheter. In contrast, in an exemplary nine-control logic die embodiment, the transition region 310 is approximately 0.5 to 0.75 catheter diameters, or between 500 and 750 µm for a 3Fr catheter. Because the scanner assembly 106 (including the transition region 310) is typically inflexible or rigid compared to the surrounding portion of the device, reducing the length of the transition region 310 results in a more agile IVUS device capable of maneuvering through complex vascular branches and producing less discomfort in the patient.

Figure 7:
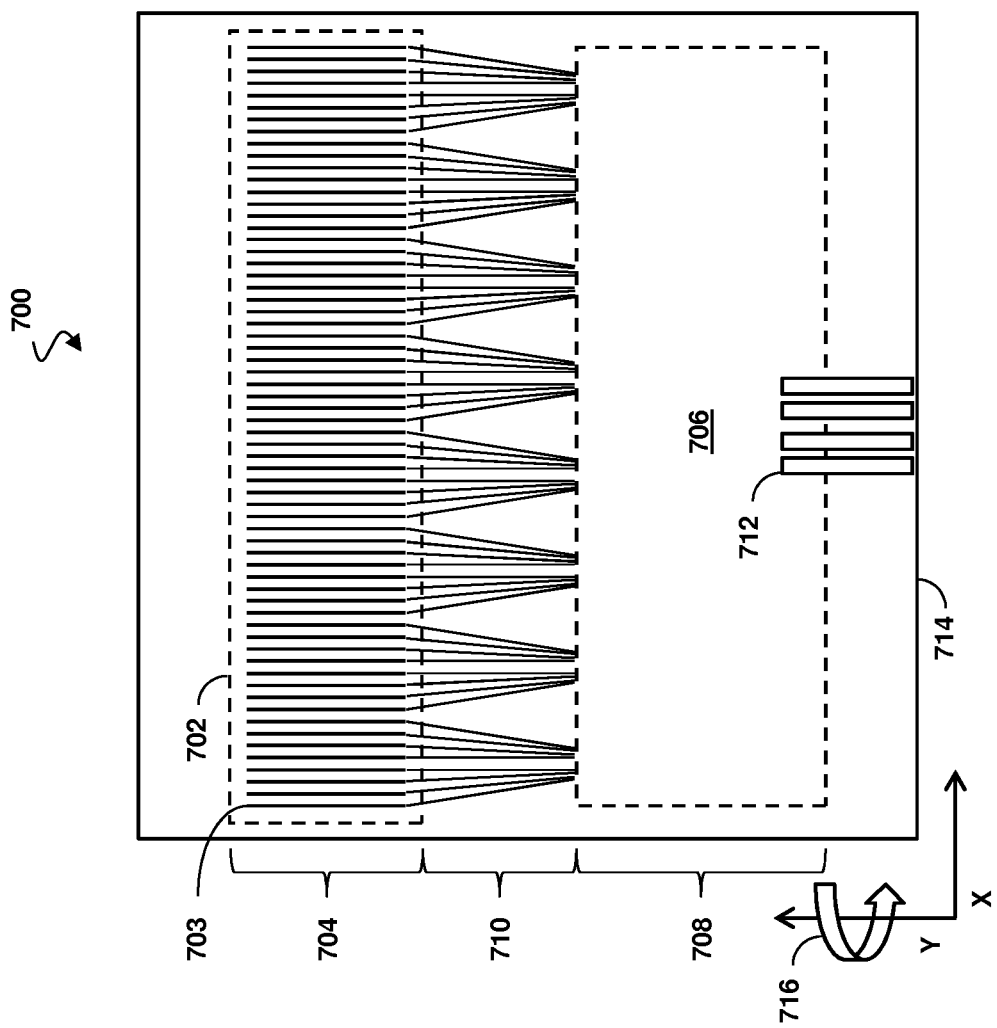
FIG. 7 is a top view of an ultrasound scanner assembly incorporating a rollable semiconductor substrate according to an embodiment of the present disclosure.

Another technique for reducing the size of the scanner assembly includes manufacturing the transducers and/or the control circuitry on a rollable semiconductor substrate. This reduces the irregularity caused by the flat transducers 312 and control logic dies 306 of the previous examples, and may reduce both the longitudinal length and the diameter of the scanner assembly. FIG. 7 is a top view of an ultrasound scanner assembly 700 incorporating a rollable semiconductor substrate according to an embodiment of the present disclosure. FIG. 7 depicts the ultrasound scanner assembly 700 in its flat form. In many respects, the ultrasound scanner assembly 700 may be substantially similar to scanner assembly 106 of FIGS. 3-6 and may include a transducer array 702 that includes any number any number and type of ultrasound transducers 703 formed in a transducer region 704. In an exemplary embodiment, the transducer array 702 includes 64 CMUT transducers 703. The ultrasound scanner assembly 700 may also include control logic circuitry 706 formed in a control region 708 with a transition region 710 disposed therebetween. The ultrasound scanner assembly 700 may also include contact pads 712 for coupling the scanner assembly 700 to a cable 114 for communication with other components of an IVUS system such as a PIM 108. However, whereas the transducers 312 and control logic dies 306 of FIG. 3, for example, are formed on a rigid substrate, the transducer array 702 and the control circuitry 706 of the present embodiment are formed on a rollable substrate 714. Thus, the elements of the scanner assembly 700 may be shaped into a curve as indicated by arrow 716 and many of the challenges involved in arranging flat components into a roughly circular profile are avoided. As a result, the transducer region 704 and the control region 708 have a more circular cross-sectional shape in the rolled configuration, as shown in more detail in the context of FIGS. 8 and 9.

Furthermore, for reasons discussed in more detail below, the overall size of the scanner assembly may be reduced 700. In brief, by eliminating the gaps between discrete dies, the diameter of the scanner assembly (and correspondingly the circumference and gauge) may be reduced. In addition, because the profiles of the control region 708 and the transducer regions 704 are similar, a shorter transition region 710 may be utilized thereby reducing the longitudinal length of the scanner assembly 700. In embodiments where the transition region 710 is not used to transition between the profiles of the control region 708 and the transducer region 704, the shorter transition region 710 may still prove useful as a sacrificial region during dicing. In an exemplary embodiment, the control region 708 measures approximately 1.5 mm in the Y direction, the transition region 710 measures approximately 1 mm in the Y direction, and the transducer region 704 measures between approximately 0.75 mm and 0.5 mm in the Y direction.

Figure 8:
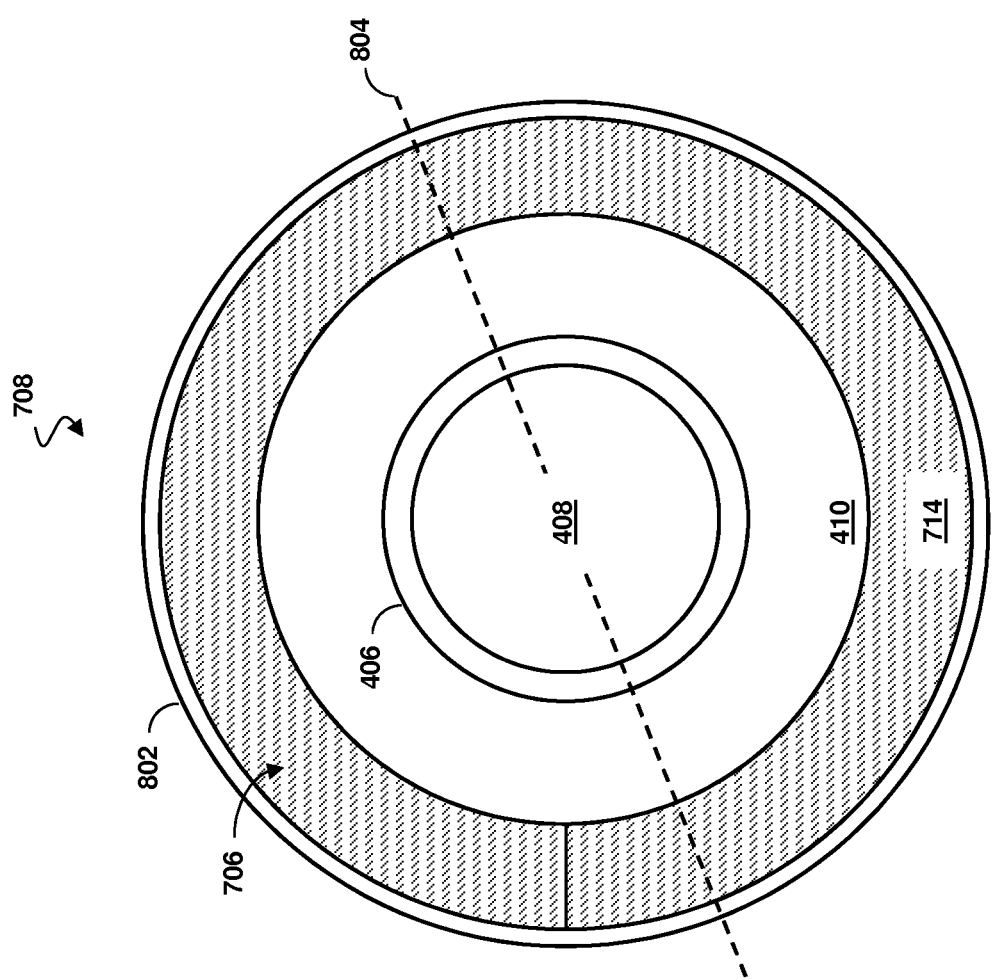
FIG. 8 is a cross-sectional view of a control region of an ultrasound scanner assembly according to an embodiment of the present disclosure.

FIG. 8 is a cross-sectional view of a control region 708 of an ultrasound scanner assembly 700 according to an embodiment of the present disclosure. The control region 708 is illustrated in its rolled form and includes the control circuitry 706 formed on a rollable semiconductor substrate 714. As can be seen, the semiconductor substrate 714 is flexed to form a cylinder and more specifically, a cylindrical toroid. The resulting cross-sectional profile of the control region 708 is substantially circular without flat regions seen in other examples. By eliminating gap space between dies and protrusions caused by flat dies, the control circuitry 706 may be packed more densely. Because dies often include reserved areas for separating dies during manufacturing (scribe lines), device density may be further improved by using a single rollable substrate 714. Similarly, dies often include insulators, pads, and other bulk that may be eliminated through the use of a rollable substrate 714.

In addition, the amount of control circuitry 706 may be reduced when compared to embodiments utilizing discrete dies. For example, partitioning the control circuitry 706 across dies often involves duplicating functionality. This duplicate logic may be avoided in embodiments where the control circuitry 706 remains together. As yet another example, partitioning the control circuitry 706 across dies often involves adding large and power hungry I/O circuitry to transmit, synchronize, and amplify signals between dies. This too may be avoided in embodiments where the control circuitry 706 remains together on the semiconductor substrate 714. Furthermore, transmitting analog signals between dies, such as echo data, may introduce noise. For these reasons and others, the control region 708 incorporating a flexible substrate 714 may be smaller and more efficient than other configurations and may provide greater imaging fidelity. In particular, the control region 708 may have a smaller diameter 804 and may have a corresponding gauge less than 3Fr.

In contrast to previous examples, by rolling the substrate 714, the devices formed on the substrate 714 (i.e., the transistors of the control circuitry 706) become curved and rearranged in a cylindrical arrangement. To account for this, the devices may be oriented on the substrate 714 in such a manner as to reduce stress and the possibility of cracking when rolled. For example, the devices may be aligned such that the gate width direction extends along the longitudinal axis of the substrate 714 in the rolled form. In some embodiments, the active regions and the gate structures of the control circuitry 706 are arranged on the outer surface of the substrate 714 when in the rolled form, whereas in other embodiments, the active regions and the gate structures are arranged on the inner surface of the substrate when in the rolled form.

In the illustrated embodiment, the control region 708 includes an outer jacket 802 used to insulate the rollable semiconductor substrate 714 and to protect the scanner assembly 700 from the environment. The insulator materials for the outer jacket 802 may be selected for their biocompatibility, durability, hydrophilic or hydrophobic properties, low-friction properties, ultrasonic permeability, and/or other suitable criteria. In various embodiments, the outer jacket 802 includes KAPTON™, polyester films, polyimide films, polyethylene napthalate films, and/or Upilex®. In further embodiments, the outer jacket 802 includes Parylene™, heat shrink tubing such as polyester or PVDF, a melt-formable layers such as Pebax® (registered trademark of Arkema) or polyethylene, and/or other suitable membrane materials. In some embodiments, the outer jacket 802 includes a flexible circuit, such as a polyimide or liquid crystal polymer-based flexible circuit. The flexible circuit may be further jacketed by a shrink fit or other jacket material. A wide variety of suitable shrink-fit materials exist including polyester and/or Pebax®. In an exemplary embodiment, a layer of the outer jacket 802 is formed with proper thickness and acoustic impedance to act as a matching layer for ultrasound signals. The matching layer typically has an acoustic impedance between that of the ultrasound transducer and the surrounding vessel and provides a smoother acoustic transition with reduced reflections.

In some instances, the control region 708 is formed around a ferrule 406 and includes an encapsulating epoxy 410 filling the space between the semiconductor substrate 714 and the ferrule 406. The lumen region 408 inside the ferrule 406 is open to allow the scanner assembly 700 to be advanced over a guide wire (not shown). The ferrule 406 may include a radiopaque material to aid in visualizing the scanner assembly 700 during a procedure.

Figure 9:
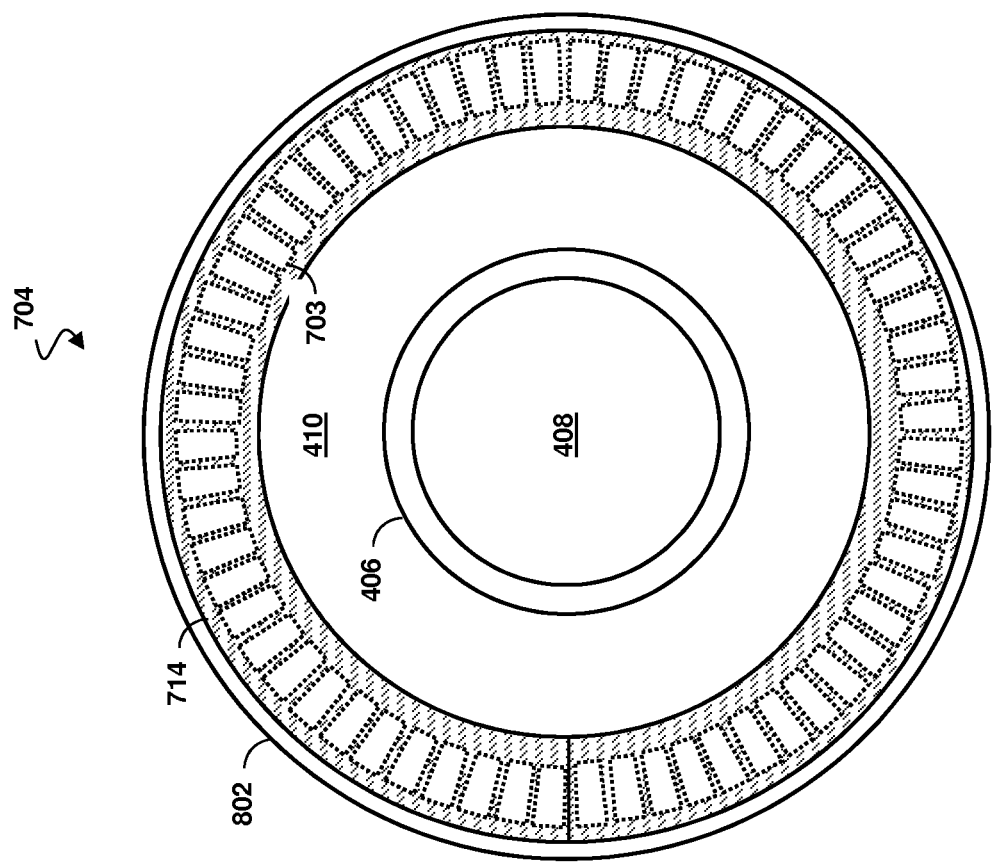
FIG. 9 is a cross-sectional view of a transducer region of an ultrasound scanner assembly according to an embodiment of the present disclosure.

FIG. 9 is a cross-sectional view of a transducer region 704 of an ultrasound scanner assembly 700 according to an embodiment of the present disclosure. The transducer region 704 is depicted in its rolled form and includes a transducer array 702 formed on a rollable semiconductor substrate 714. The transducer array 702 includes any number any number and type of ultrasound transducers 703, and in an exemplary embodiment includes 64 CMUT transducers. As in the control region 708, the semiconductor substrate 714 is flexed to form a cylinder or cylindrical toroid and the resulting cross-sectional profile of the transducer region 704 is substantially circular. Similar to the control region 708, the transducers of the transducer array 702 become curved and take on a cylindrical arrangement. In an exemplary embodiment, the transducers of the transducer array 702 are arranged on the outer surface of the substrate 714 when in the rolled form.

Figure 10:
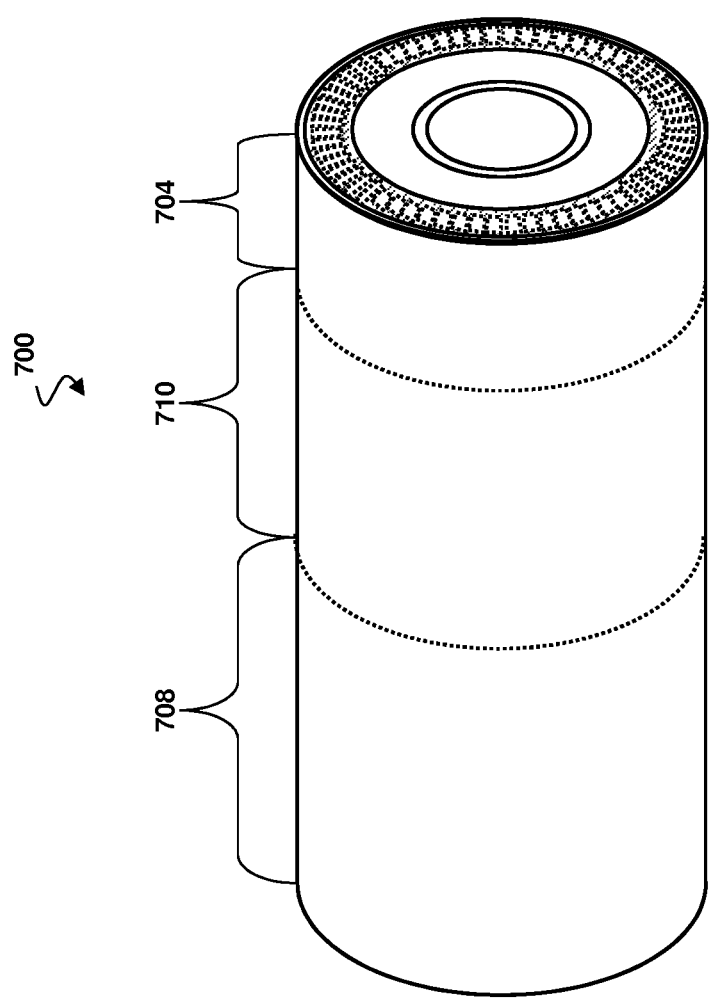
FIG. 10 is a longitudinal perspective view of a portion of an ultrasound scanner assembly depicted in its rolled form according to an embodiment of the present disclosure.

FIG. 10 is a longitudinal perspective view of a portion of an ultrasound scanner assembly 700 depicted in its rolled form according to an embodiment of the present disclosure. The scanner assembly 700 includes a transition region 710 located between the transducer region 704 and the control region 708. As can be seen, the cross-sectional profiles of the transducer region 704 and the control region 708 are similar and thus the transition region 710 may be shorter in the longitudinal direction as compared to the previous examples. For a variety of reasons, including those discussed above, the gauge or thickness of the rolled scanner assembly 700 may be less than that of other configurations. For example, in various embodiments, the scanner assembly 700 is between 2-3Fr and, in a specific embodiment, the scanner assembly 700 measures approximately 2Fr.

Figure 11:
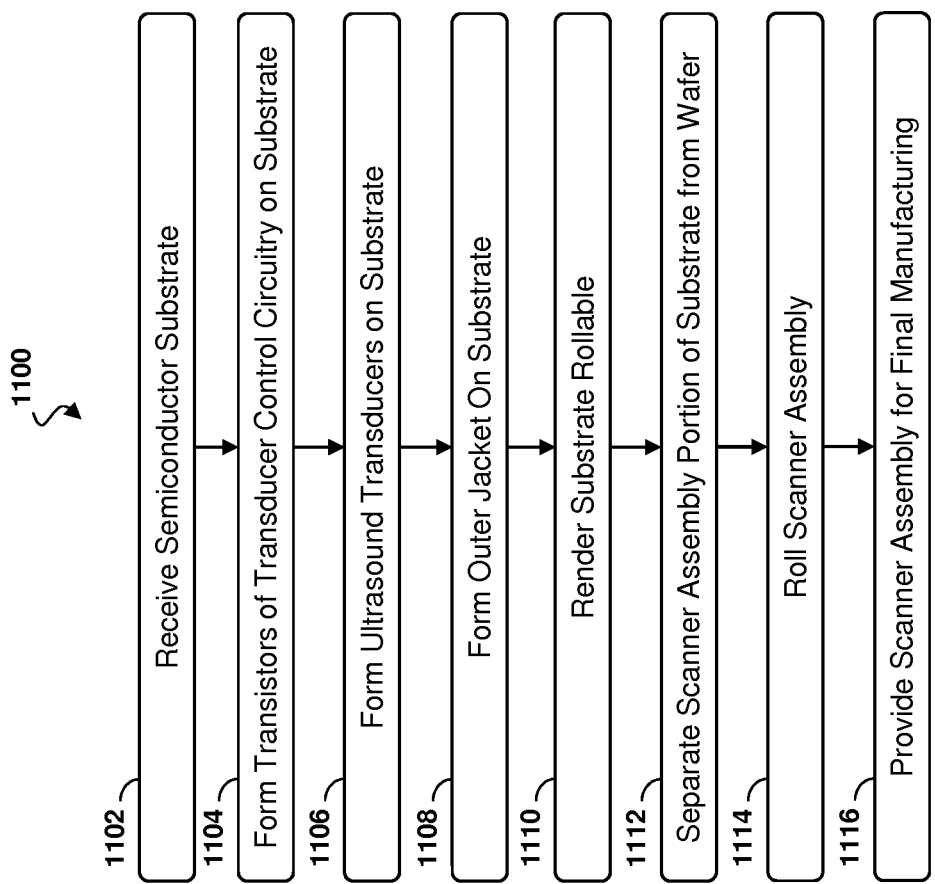
FIG. 11 is a flow diagram of the method of manufacturing an ultrasound scanner assembly according to an embodiment of the present disclosure.

A method of forming an ultrasound scanner assembly 700 incorporating a rollable semiconductor substrate 714 is described with reference to FIGS. 11-17. FIG. 11 is a flow diagram of the method 1100 of manufacturing the ultrasound scanner assembly 700 according to an embodiment of the present disclosure. It is understood that additional steps can be provided before, during, and after the steps of method 1100 and that some of the steps described can be replaced or eliminated for other embodiments of the method. FIGS. 12-16 are cross-sectional views of a scanner assembly 700 being manufactured by the method according to an embodiment of the present disclosure. FIGS. 12-16 each show transducer control circuitry 706 being manufactured in a control region 708 and a transducer array 702 being manufactured in a transducer region 704. FIG. 17 is a top view of a scanner assembly 700 formed on a wafer undergoing the method of manufacturing according to an embodiment of the present disclosure.

Referring to block 1102 of FIG. 11 and to FIG. 12, a semiconductor substrate 714 is received. Substrate 714 may be any base material on which processing is conducted to produce layers of materials, pattern features, and/or integrated circuits such as those used to manufacture transducer control circuitry 706. Examples of semiconductor substrates include a bulk silicon substrate, an elementary semiconductor substrate such as a silicon or germanium substrate, a compound semiconductor substrate such as a silicon germanium substrate, an alloy semiconductor substrate, and substrates including non-semiconductor materials such as glass and quartz.

Referring to block 1104 of FIG. 11 and referring still to FIG. 12, transistors of the control circuitry 706 are formed on the substrate 714 in the control region 708. An exemplary process for forming the transistors includes growing a pad oxide layer over the substrate, depositing a nitride layer by chemical vapor deposition, performing a reactive ion etching to form a trench, growing a shallow trench isolation feature oxide, chemical-mechanical planarization, channel implantation, formation of a gate oxide, polysilicon deposition, etching to form a gate structure, source-drain implantation, forming of sidewall spacers, performing a self-aligned silicide process, forming one or more interconnect layers, forming a pad layer, and/or other fabrication processes known to one of skill in the art. In some instances, the process for forming the control circuitry 706 produces gate structures 1202, shallow trench isolation features 1204, conductive interconnects 1206, and insulator layers 1208.

Referring to block 1106 of FIG. 11 and to FIGS. 13-15, one or more transducers of the transducer array 702 are formed on the substrate 714. The present disclosure is not limited to any particular transducer technology, and while the illustrated embodiment includes CMUT transducers, other embodiments incorporate thin-film PZT transducers, PMUT transducers, and/or other transducer types. Referring to FIG. 13, in one example, CMUT transducers are formed in block 1106 by depositing a dielectric layer 1302 on the substrate 714 and depositing a sacrificial layer 1304, such as a polysilicon layer, on the dielectric layer 1302 to define the CMUT vacuum gap, which acts as a resonance chamber. Referring to FIG. 14, further dielectric material 1402 is deposited over the sacrificial layer 1304 with holes formed therein to allow the sacrificial layer 1304 to be etched. Referring to FIG. 15, the sacrificial layer 1304 is etched away from underneath the dielectric and the holes are filled with additional dielectric material 1402. This may be performed in a vacuum so that the remaining cavity is a vacuum gap 1502 within the dielectric formation of 1302 and 1402.

The material over the vacuum gap 1502 is referred to as a diaphragm 1504 or drumhead and is free to deflect into the vacuum gap 1502. An electrode 1506 is formed over the vacuum gap that together with a conductive region of the substrate 714 form a parallel plate capacitor. Deflection of the diaphragm 1504 and the electrode 1506 into the vacuum gap, such as deflection caused by an ultrasonic wave, changes the electrical behavior of the capacitor. These changes can be measured in order to determine properties of the wave that caused them. One or more interconnect layers 1206 and/or passivation layers 1208 may then be formed over the electrode 1506.

Referring to block 1108 of FIG. 11 and to FIG. 15, a polymer coating such as the outer jacket 802 described in FIG. 8 may be formed on the substrate 714 and insulates the control circuitry 706 and the transducer array 702. Additionally or in the alternative, the outer jacket 802 may be formed over the substrate 714 after the rolling of the substrate 714 during the final assembly in block 1116, described below.

Figure 16:
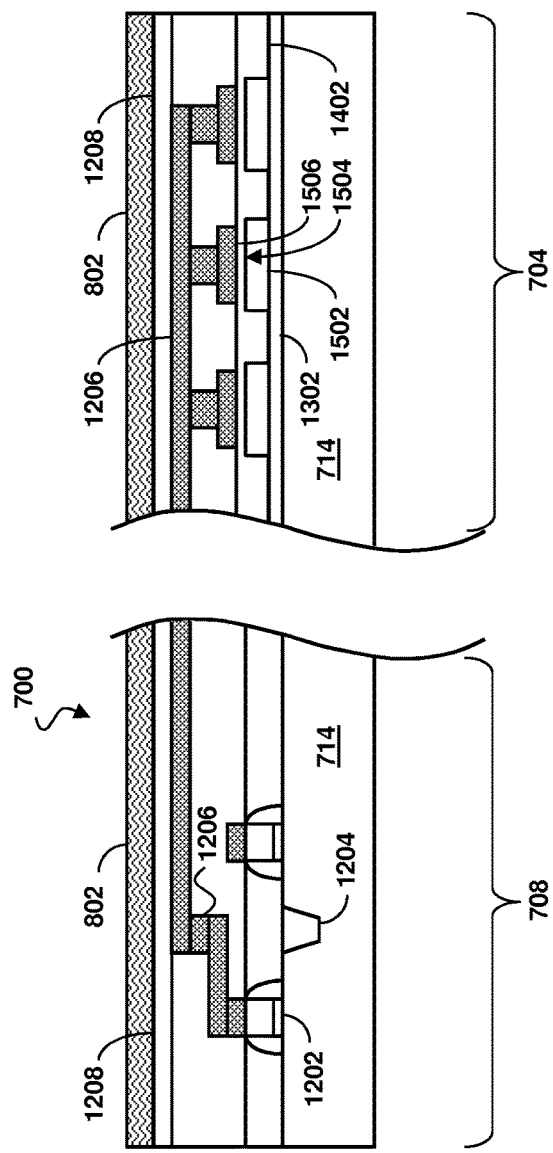
Figure 17:
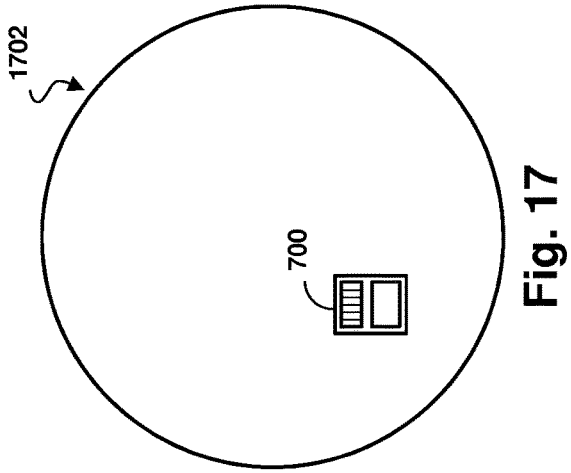
FIG. 17 is a top view of a scanner assembly formed on a wafer undergoing the method of manufacturing according to an embodiment of the present disclosure.

Referring to block 1110 of FIG. 11 and to FIG. 16, the substrate 714 is made rollable. In other words, while the finished substrate 714 may be flexible enough to be rolled, the substrate 714 in its initial form may be rigid for easier manufacturing of the transducer array 702 and the control circuitry 706. In some embodiments, the substrate 714 is made rollable by performing a thinning process. For example, in some embodiments, thinning the substrate 714 to a thickness of approximately 10 µm or less results in a substrate 714 that is flexible enough to be rolled. Suitable thinning processes include mechanical grinding, wet or dry etching, chemical-mechanical polishing, fracturing, and/or otherwise thinning the substrate 714. In an embodiment, the wafer thinning process includes mechanical grinding of the substrate 714. Mechanical grinding uses abrasive force to remove substrate material. In another embodiment, the wafer thinning process includes chemical-mechanical polishing (CMP). In an exemplary CMP process, a polishing pad is installed on a rotating platen. A slurry of reactive compounds such as NH4OH and/or abrasive particles such as silica (SiO2), alumina (Al2O3), and ceria (CeO2) is dispensed on the polishing pad. The substrate 714, secured in a CMP chuck, is forced against the polishing pad as both the platen and the CMP chuck rotate. The reactants in the slurry loosen atomic bonds within the surface of the substrate 714, while the mechanical abrasion removes the loosened material. CMP is typically slower than purely mechanical grinding but produces less damage to the substrate 714.

In some embodiments, the substrate 714 includes one or more buried layers to control the thinning of the substrate 714. For example, in an embodiment, the substrate 714 includes a dielectric layer that acts as a stop layer during a mechanical grinding process. In a further example, the substrate 714 includes a buried dielectric layer (e.g., a buried oxide layer) that acts as an etch stop layer during a chemical etching process. In yet a further example, the substrate 714 includes a cleavage layer that separates from the remainder of the substrate 714 during a mechanical separation process.

Referring to block 1112 of FIG. 11 and to FIG. 17, the transducer array 702 and the control circuitry 706 of the scanner assembly 700 are singulated from a wafer 1702. As can be seen, several scanner assemblies 700 can be formed on a single wafer 1702. For example, approximately two thousand scanner assemblies 700 each measuring 10 mm² may be formed on a single 8" wafer 1702. Before being rolled, the scanner assemblies 700 are separated using techniques that may include saw dicing, mechanical cutting, laser cutting, physical force, and/or other suitable singulation techniques.

Referring to block 1114 of FIG. 11, the scanner assembly 700 is rolled to have a substantially cylindrical form as shown in FIGS. 8-10. Because the rolling process curves the transistors of the control circuitry 706 and the transducers 703 of the transducer array 702, flat areas and other irregularities are reduced. In some embodiments, rolling includes applying a retaining structure 416 before the scanner assembly 700 is shaped into the substantially cylindrical form.

Referring to block 1116 of FIG. 11, the scanner assembly 700 is provided to a finishing facility for final assembly, which may include applying an encapsulating epoxy 410, attaching the cable 114, and/or sealing the scanner assembly 700. Thus, the use of a rollable semiconductor substrate 714 in method 1100 eliminates the complexity and yield loss associated with dicing tiny components and bonding them to a flexible interconnect. As a result, the manufacturing technique simplifies assembly, reduces assembly time, and improves both yield and device reliability.

Figure 18A:
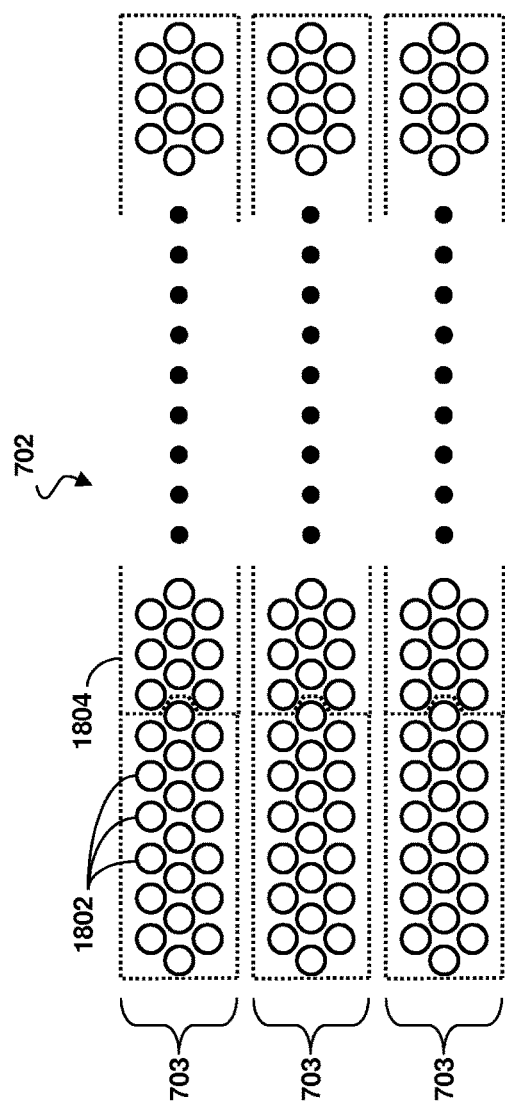
FIGS. 18A and 18B are top views of a portion of a transducer array according to an embodiment of the present disclosure.
Figure 18B:
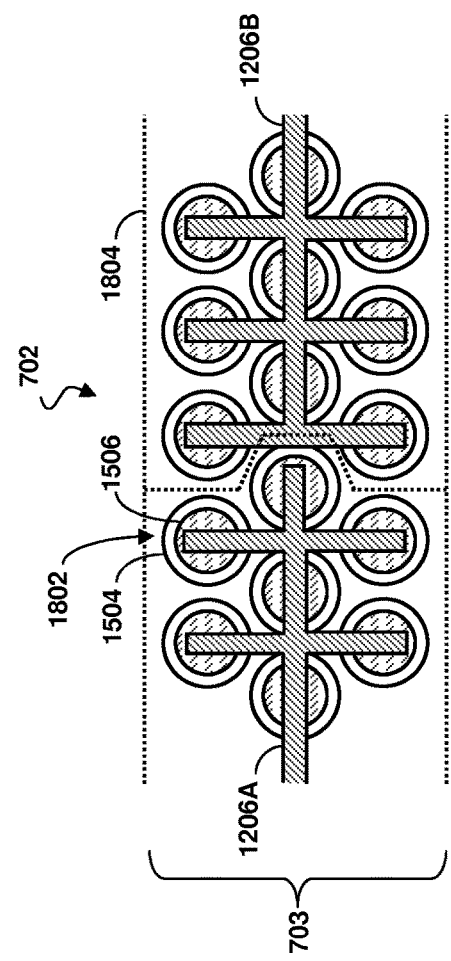
Figure 19:
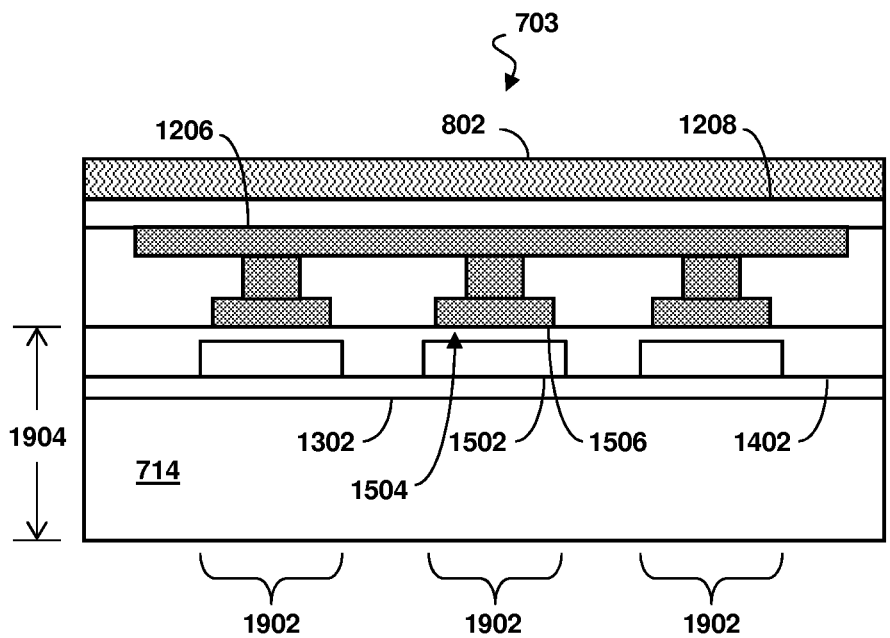
FIG. 19 is a cross-sectional view of a portion of a transducer incorporating an array of CMUT elements according to an embodiment of the present disclosure.
Figure 20:
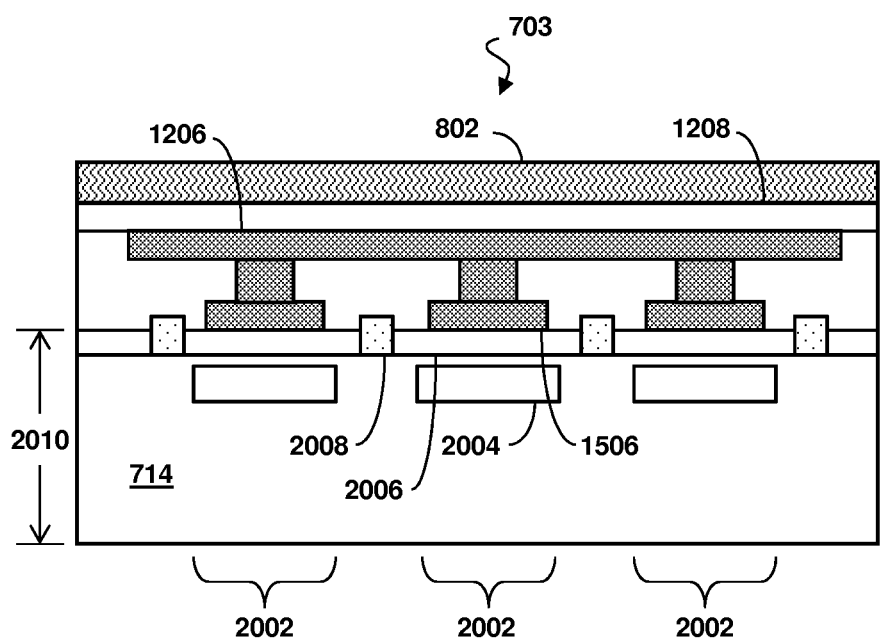
FIG. 20 is a cross-sectional view of a portion of a transducer incorporating an array of piezoelectric elements according to an embodiment of the present disclosure.

As disclosed above, the scanner assembly 700 may incorporate any suitable ultrasound transducer technology, including the CMUT transducer 703 illustrated in FIG. 16. Suitable transducers 703 are illustrated in further detail in FIGS. 18A, 18B, 19, and 20. FIGS. 18A and 18B are top views of a portion of a transducer array 702 according to an embodiment of the present disclosure. FIG. 18B is an enlarged view of the portion. FIG. 19 is a cross-sectional view of a portion of a transducer 703 incorporating an array of CMUT elements 1902 according to an embodiment of the present disclosure. FIG. 20 is a cross-sectional view of a portion of a transducer 703 incorporating an array of piezoelectric elements 2002 according to an embodiment of the present disclosure.

Referring first to FIGS. 18A and 18B, in the illustrated embodiment, each transducer 703 of the transducer array 702 includes an array of transducer elements 1802. Each element 1802 is itself a transducer operable to generate a waveform by vibrating a diaphragm 1504 (i.e., a drumhead) and to produce an electrical signal in response to a received waveform. In that regard, each element 1802 may include a diaphragm 1504, a chamber such as a vacuum gap 1502, an associated electrode 1506, and/or any other ancillary structure. Because of the limited displacement of each element 1802, each transducer 703 may include multiple elements 1802 electrically connected in parallel to increase the effective surface area. For example, the electrodes 1506 of multiple diaphragms 1504 may be connected by a common interconnect (e.g., interconnects 1206A and 1206B). In this way, the transducers 703 can compensate for a thinner substrate 714 and correspondingly shallower vacuum gaps. In the illustrated embodiment, each diaphragm 1504 is substantially circular with a diameter of approximately 10 µm, although it is understood in further embodiments the transducers 703 include other sizes and shapes of diaphragm 1504. In the interest of clarity, the number of elements 1802 has been reduced, and while each transducer 703 may include any number of elements 1802, in an exemplary embodiment, each transducer 703 includes approximately 100 elements.

In addition to providing a large effective surface area, an array of elements 1802 can be tuned to more than one frequency by adjusting the number of elements 1802 operating in unison. An array can also produce specialized waveforms by adjusting the firing sequence of the elements 1802. Accordingly, in some embodiments, elements 1802 of a transducer 703 are arranged into groups (indicated by dashed boxes 1804). While the elements 1802 of each group are electrically connected in parallel and thus operate in unison, the groups can be independently controlled or addressed to produce a number of different ultrasonic waveforms at a number of different characteristic frequencies. Thus, a single transducer 703 can support multiple imaging modes, with common modes including both 20 MHz and 40 MHz modes.

Referring now to FIG. 19, a portion of a transducer 703 is shown. In the embodiment, the transducer 702 includes CMUT transducer elements 1902. The three illustrated elements each include a vacuum gap 1502 defined by a dielectric layer 1302 formed on the substrate 714, a diaphragm 1504 formed over the vacuum gap 1502, an electrode 1506 formed over the diaphragm, and an interconnect 1206 electrically coupling the diaphragms 1504 to other diaphragms 1504 and to the control circuitry (not shown).

As can be seen, the CMUT transducer elements 1902 are well suited for the rollable substrate 714 because their overall profile can be quite thin. For example, in an embodiment, the combined thickness 1904 of the diaphragm 1504, the vacuum gap 1502, and the substrate 714 is less than or substantially equal to 10 μm. In the embodiment, the diaphragm 1504 has a thickness of approximately 1 μm, and the vacuum gap 1502 has a thickness of approximately 0.1 μm.

Referring to FIG. 20, a portion of another transducer 702 that includes piezoelectric transducer elements 2002 is shown. The piezoelectric elements 2002 are a suitable substitute for the CMUT elements 1902 described above and, when arranged in an array to form a transducer 703 may have a top view substantially similar to that of FIGS. 18A and 18B.

When viewed in the cross-section, the piezoelectric elements 2002 each include a chamber 2004 formed in the substrate 714. A piezoelectric thin-film 2006 is formed over the chamber 2004.

Similar to the CMUT diaphragm 1504, the piezoelectric elements 2002 can be quite thin. For example, in an embodiment, the combined thickness 2008 of the piezoelectric thin-film 2006 and the substrate 714 containing the chamber 2004 have a combined thickness between approximately 5 μm and approximately 10 μm, with the piezoelectric thin-film 2006 having a thickness between approximately 1 μm and approximately 2 μm.

By connecting several elements in parallel, the embodiments of FIGS. 19 and 20 provide an effective element size that is much greater than the individual diaphragm size. This allows the transducer to provide a more powerful ultrasonic signal while transmitting and to produce a stronger electrical signal while receiving. In addition, the operational frequency of a transducer can be tuned by adjusting the number of elements operating in parallel. The result is a more sensitive transducer in a smaller package.

Thus, the present disclosure provides an improved IVUS device with a scanner assembly that is designed to be both smaller and more uniform, and provides a method for manufacturing the scanner assembly improves yield and takes much of the complexity out of the manufacturing.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging device, comprising:
   a flexible elongate member configured to be positioned within a vessel of a patient; and
   an ultrasound scanner assembly disposed at a distal portion of the flexible elongate member and including a silicon substrate, the silicon substrate comprising a plurality of transistors and a plurality of ultrasound transducers formed thereupon, the silicon substrate comprising a first end and an opposite, second end,
   wherein the silicon substrate is curved to have a substantially cylindrical form when the ultrasound scanner assembly is in a rolled form such that the first end and second end are adjacent to one another, wherein the silicon substrate is continuous around a circumference of the substantially cylindrical form between the first and second ends,
   wherein the plurality of transistors are arranged in a cylindrical arrangement when the ultrasound scanner assembly is in the rolled form, and
   wherein a thickness of the silicon substrate renders the silicon substrate flexible to be curved into the substantially cylindrical form.

2. The device of claim 1, wherein the plurality of transistors includes transducer control circuitry and the plurality of ultrasound transducers are formed upon the silicon substrate and electrically coupled to the transducer control circuitry, wherein the plurality of ultrasound transducers are arranged in a cylindrical arrangement when the ultrasound scanner assembly is in the rolled form.

3. The device of claim 2, wherein each transducer of the plurality of ultrasound transducers includes a plurality of transducer elements electrically connected in parallel.

4. The device of claim 2, wherein each transducer of the plurality of ultrasound transducers includes at least two groups of transducer elements, wherein the at least two groups of transducer elements are independently addressable by the transducer control circuitry.

5. The device of claim 2 further comprising an insulating layer formed over the plurality of transistors and the plurality of ultrasound transducers such that the insulating layer is outside the plurality of transistors and the plurality of ultrasound transducers when the ultrasound scanner assembly is in the rolled form.

6. The device of claim 2, wherein the plurality of ultrasound transducers includes a CMUT transducer comprising:
   a dielectric material formed over the silicon substrate;
   a vacuum gap formed within the dielectric material;
   a diaphragm formed over the vacuum gap; and
   an electrode formed over the diaphragm.

7. The device of claim 6, wherein the diaphragm, the vacuum gap, and the silicon substrate have a combined thickness of less than or substantially equal to 10 μm.

8. The device of claim 6, wherein the vacuum gap has a thickness substantially equal to 0.1 μm.

9. The device of claim 6, wherein the diaphragm has a thickness substantially equal to 1 μm.

10. The device of claim 6, wherein the plurality of ultrasound transducers includes a piezoelectric micromachined ultrasound transducer (PMUT) comprising:
    a chamber formed within the silicon substrate; and
    a piezoelectric film formed over the chamber.

11. The device of claim 10, wherein the piezoelectric film and the silicon substrate have a combined thickness of between approximately 5 µm and approximately 10 µm.

12. The device of claim 1, wherein the plurality of transducer elements includes CMUT transducer elements.

13. The device of claim 1, wherein the plurality of transducer elements includes thin-film piezoelectric transducer elements.

14. The device of claim 1, wherein the silicon substrate further includes germanium.

15. The device of claim 14, wherein the thickness of the silicon substrate is less than or substantially equal to 10 µm as measured when the ultrasound scanner assembly is in a flat form.

16. The device of claim 1, wherein the ultrasound scanner assembly further includes a ferrule disposed within the substantially cylindrical form of the silicon substrate when the ultrasound scanner assembly is in the rolled form.

17. The device of claim 16 further comprising an epoxy disposed between the ferrule and the silicon substrate.

18. The device of claim 16, wherein the ferrule includes an inner lumen adapted to pass a guide wire.

19. The device of claim 1, wherein the plurality of transistors each includes a gate structure and a gate width direction extending along a longitudinal axis of the substantially cylindrical form.

\* \* \* \* \*